(12) United States Patent
Kammerstetter et al.

(10) Patent No.: US 10,094,378 B2
(45) Date of Patent: Oct. 9, 2018

(54) SYSTEM FOR MEASURING TEMPORALLY RESOLVED THROUGH-FLOW PROCESSES OF FLUIDS

(71) Applicant: AVL LIST GMBH, Graz (AT)

(72) Inventors: Heribert Kammerstetter, Salzburg (AT); Christian Thomas Berger, Graz (AT); Otfried Derschmidt, Graz (AT); Manfred Pross, Graz (AT); Martin Duerrwaechter, Aachen (DE); Herwig Breitwieser, Graz (AT); Othmar Bernhard, Spielfeld (AT)

(73) Assignee: AVL LIST GMBH, Graz (AT)

( * ) Notice: Subject to any disclaimer, the term of this patent is extended or adjusted under 35 U.S.C. 154(b) by 276 days.

(21) Appl. No.: 15/075,207

(22) Filed: Mar. 21, 2016

(65) Prior Publication Data
US 2016/0281708 A1   Sep. 29, 2016

(30) Foreign Application Priority Data

Mar. 24, 2015 (AT) .................................. A 168/2015

(51) Int. Cl.
*F04C 2/00* (2006.01)
*F04C 2/08* (2006.01)
(Continued)

(52) U.S. Cl.
CPC ................ *F04C 2/084* (2013.01); *G01F 1/50* (2013.01); *G01F 3/24* (2013.01); *G01F 5/005* (2013.01);
(Continued)

(58) Field of Classification Search
CPC ........ F04C 2/084; G01F 15/02; G01F 15/185; G01F 1/50; G01F 3/10; G01F 3/24; G01F 5/005; G01N 11/08
See application file for complete search history.

(56) References Cited

U.S. PATENT DOCUMENTS 3,618,383 A * 11/1971 Holden .................... F02D 1/00
                                                          137/101
3,633,420 A *  1/1972 Holzem ............... G01F 15/026
                                                          388/906
(Continued)

FOREIGN PATENT DOCUMENTS

DE        1 798 080 B1   10/1973
DE     103 31 228 B3      1/2005
(Continued)

*Primary Examiner* — Francis C Gray
(74) *Attorney, Agent, or Firm* — Norman B. Thot

(57) ABSTRACT

A system for measuring temporally resolved through-flow processes of a fluid. The system includes an inlet, a main line comprising a line section, an outlet fluidically connected with the inlet via the main line, a displacement device arranged in the main line, a circuitous line which branches off the main line between the inlet and the displacement device and to enter the main line between the displacement device and the outlet, a pressure difference transducer arranged in the circuitous line, an evaluation and control unit which controls the displacement device, and a bypass line comprising a pump and a sensor. The bypass line branches off from the main line or from the circuitous line and ends at a same side of the displacement device and the pressure difference transducer to bypass the line section or the circuitous line from which the bypass line branches off.

14 Claims, 2 Drawing Sheets

(51) Int. Cl.
    *G01F 1/50*      (2006.01)
    *G01F 5/00*      (2006.01)
    *G01F 15/18*     (2006.01)
    *G01F 15/02*     (2006.01)
    *G01F 3/24*      (2006.01)
    *G01N 11/08*     (2006.01)
    *G01F 3/10*      (2006.01)

(52) U.S. Cl.
    CPC ............ *G01F 15/02* (2013.01); *G01F 15/185* (2013.01); *G01N 11/08* (2013.01); *G01F 3/10* (2013.01)

(56) References Cited

U.S. PATENT DOCUMENTS

| | | | | |
|---|---|---|---|---|
| 4,193,299 | A | * | 3/1980 | Holzem ................ G01F 15/026 73/199 |
| H001479 | H | * | 9/1995 | Paulonis .................... 422/82.01 |
| 7,254,993 | B2 | * | 8/2007 | Metzler .................. A62C 99/00 73/114.47 |
| 7,905,141 | B2 | * | 3/2011 | Wakamatsu ............. G01F 1/38 73/239 |
| 7,905,142 | B2 | * | 3/2011 | Wakamatsu ............. G01F 3/10 73/239 |
| 2004/0060345 | A1 | | 4/2004 | Eggen et al. |
| 2006/0201244 | A1 | | 9/2006 | Metzler et al. |
| 2010/0043568 | A1 | | 2/2010 | Wakamatsu |
| 2012/0297867 | A1 | | 11/2012 | Kammerstetter et al. |
| 2015/0369646 | A1 | | 12/2015 | Derschmidt |
| 2016/0187172 | A1 | * | 6/2016 | Gottlieb .................. G01F 1/667 73/152.32 |

FOREIGN PATENT DOCUMENTS

| | | |
|---|---|---|
| DE | 10 2009 058 932 A1 | 6/2011 |
| EP | 2 128 574 A1 | 12/2009 |
| FR | 1309888 | 11/1962 |
| GB | 2 000 228 A | 1/1979 |
| GB | 2 259 368 A | 3/1993 |
| WO | WO 02/052243 A1 | 7/2002 |
| WO | WO 2005/005935 A1 | 1/2005 |
| WO | WO 2014/118045 A1 | 8/2014 |
| WO | WO 2014/206767 A1 | 12/2014 |

* cited by examiner

SYSTEM FOR MEASURING TEMPORALLY RESOLVED THROUGH-FLOW PROCESSES OF FLUIDS

CROSS REFERENCE TO PRIOR APPLICATIONS

Priority is claimed to Austrian Patent Application No. A 168/2015, filed Mar. 24, 2015. The entire disclosure of said application is incorporated by reference herein.

FIELD

The present invention relates to a system for measuring temporally resolved through-flow processes of fluids, having an inlet, an outlet, and a through-flow meter arranged between the inlet and the outlet, as well as a system for measuring temporally resolved through-flow processes of fluids, having an inlet, an outlet which is fluidically connected with the inlet via a main line, a displacement device adapted to be driven and arranged in the main line, a circuitous line which branches off the main line between the inlet and the displacement device and enters the main line between the displacement device and the outlet, a pressure difference transducer which is arranged in the circuitous line, and an evaluation and control unit via which the displacement device adapted to be driven is controllable as a function of the pressure difference prevailing at the translational pressure difference transducer.

BACKGROUND

Such systems have previously been described and have been used for injection quantity measurements in internal combustion engines.

DE-AS 1 798 080 thus describes an electronically controlled through-flow meter having an inlet and an outlet between which a rotational displacement device configured as a gear pump is arranged, and a piston arranged in a measuring chamber in a line extending parallel to the displacement device. The displacement of the piston in the measuring chamber is measured by an optical sensor to determine the through-flow rate. On the basis of this signal, the rotational speed of the gear pump is continuously readjusted via an evaluation and control unit so that the piston is, if possible, always returned to its initial position so that only small flows are produced in the circuitous line. The through-flow within a predetermined time interval is calculated on the basis of the number of rotations or partial rotations of the gear pump measured by an encoder as well as the known volume flow of the gear pump during one rotation.

A through-flow meter of such a design is also described in DE 103 31 228 B3. For determining the exact injection discharge rates, the gear pump is adjusted to a constant rotational speed before the injection process is started so that the movement of the piston is subsequently measured and used to determine the injection discharge rates. A pressure sensor and a temperature sensor are additionally arranged in the measuring chamber, the measuring values of which are also supplied to the computing unit to calculate and correct the injection discharge rates.

It has, however, turned out that determining of the injection discharge rates is still subject to minor errors which are attributable to variations of the viscosity or the density of the measured fluid that have thus far not been considered.

SUMMARY

An aspect of the present invention is to provide a system to measure temporally resolved through-flow processes of fluids via which through-flow rates can be calculated even more precisely. An aspect of the present invention is in particular to consider additional information with regard to the respective physical properties of the fluid without negatively affecting the actual results measured by the through-flow meter, which might be the case if a density sensor were installed in the main line or in the circuitous line of the meter.

In an embodiment, the present invention provides a system for measuring temporally resolved through-flow processes of a fluid. The system includes an inlet, a main line comprising a line section, an outlet fluidically connected with the inlet via the main line, a displacement device configured to be driven in and arranged in the main line, a circuitous line which branches off the main line between the inlet and the displacement device and to enter the main line between the displacement device and the outlet, a pressure difference transducer arranged in the circuitous line, an evaluation and control unit configured to control the displacement device as a function of a pressure difference prevailing at the pressure difference transducer, and a bypass line comprising a pump and a sensor connected in series. The sensor is configured to measure a physical property or a chemical property of the fluid. The bypass line is arranged to branch off from the main line or from the circuitous line and to end at a same side of the displacement device and the pressure difference transducer so as to bypass the line section of the main line or the circuitous line from which the bypass line branches off.

BRIEF DESCRIPTION OF THE DRAWINGS

The present invention is described in greater detail below on the basis of embodiments and of the drawings in which.

DETAILED DESCRIPTION

Figure 1:
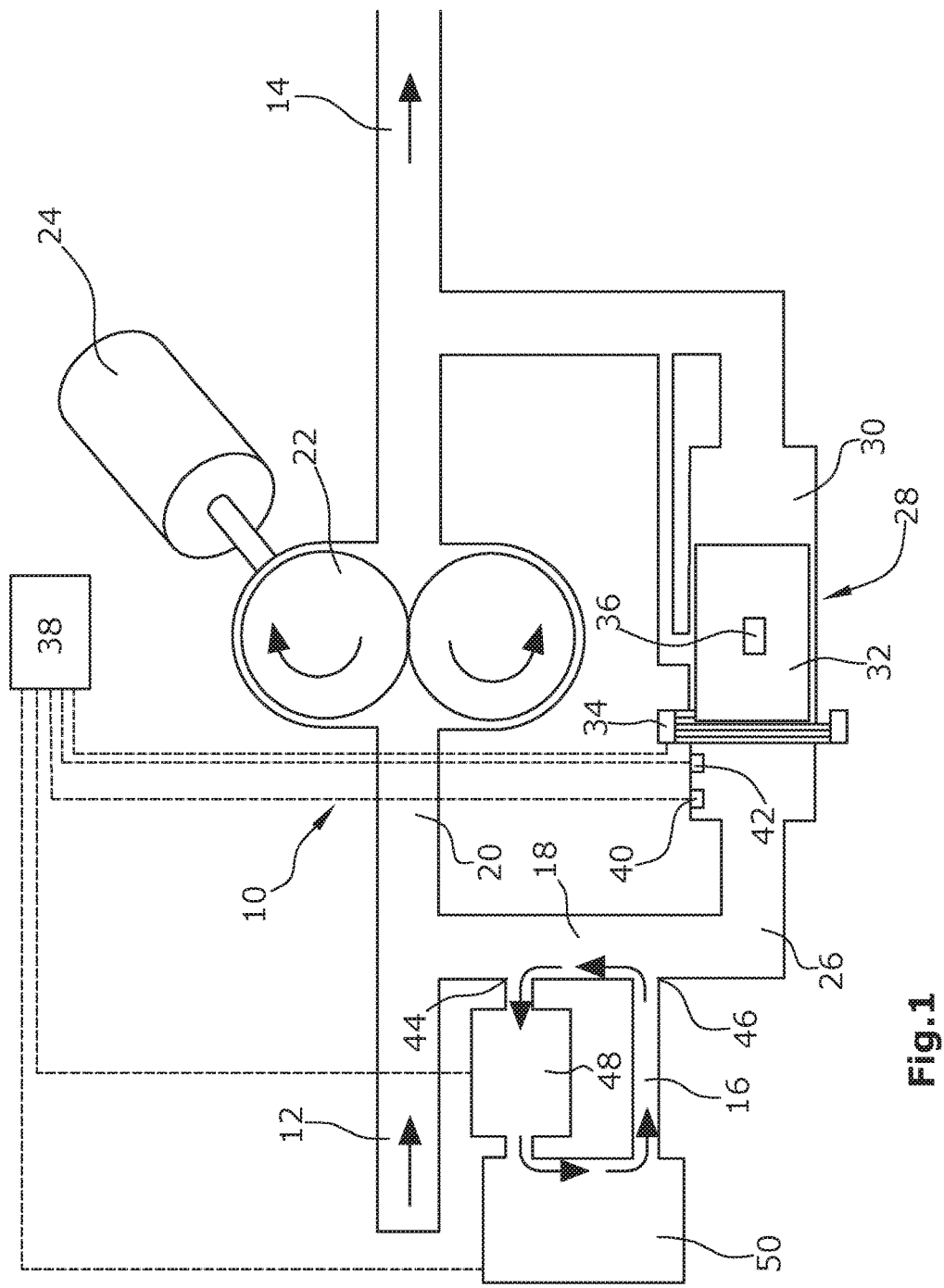
FIG. 1 shows a schematic representation of the basic configuration of a system according to the present invention for measuring temporally resolved through-flow processes of fluids.

Due to the fact that a line section of the through-flow meter is adapted to be passed by a fluid via a bypass line in which a pump and a sensor for measuring a physical or a chemical property of the delivered fluid are arranged in series, an additional physical variable, such as the density or the viscosity of the measured fluid, can be taken into account by a through-flow meter during determination of the through-flow. The pump provides a flow through sensor for this purpose. The arrangement in the bypass line prevents effects on the through-flow meter.

When a system having a through-flow meter with a pressure difference transducer connected in parallel to a displacement device is used, a bypass line branches off the main line or the circuitous line of the through-flow meter and ends at the same side of the displacement device and the pressure difference transducer, thus bypassing a line section of the main line or the circuitous line from which the bypass line branches off, wherein, in the bypass line, a pump and a sensor for measuring a physical or a chemical property of the delivered fluid are connected in series. Independent of a through-flow in the main line or the circuitous line, a through-flow in the bypass line is thus provided which provides a proper functioning of the sensor arranged in the bypass line. An adequate through-flow through the sensor is above all provided, which would otherwise have had to be provided by an external energy supply if the sensor were installed in the main line or the circuitous line, which would have an effect on the measuring data of the through-flow meter. Density sensors in particular require such a through-flow to supply correct measuring values. The values of the corresponding sensor may either merely serve for evaluation purposes or as an additional controlled variable. Even more accurate measuring results of such a through-flow meter can be obtained by using this system according to the present invention.

In an embodiment of the present invention, the bypass line can, for example, branch off the circuitous line between the inlet and the pressure difference transducer and end there. This position is very good to access so that short connecting lines are sufficient. An influence on the measurement is also prevented since the medium can be directly circulated without a flow being produced at the measuring chamber.

In an embodiment of the present invention, the sensor can, for example, be a density sensor or a viscosity sensor so that their measuring values supply additional information which can be taken into account in the results of the through-flow meter for the purpose of improving the calculated through-flow. These sensors can be configured as MEMS sensors which operate, for example, according to the Coriolis principle.

In an embodiment of the present invention, the pump can, for example, be a pump which delivers in a pulsation-free manner. A completely pulsation-free delivery entirely precludes an influence on the pressure difference transducer and thus the measuring results of the through-flow meter. Incorrect measurements of the density sensors are additionally avoided, which sensors, in particular when configured as MEMS sensors, would be induced to oscillate by the oscillation of the measuring fluid, whereby their measuring results would be falsified.

In an embodiment of the present invention, the pump delivering in a pulsation-free manner can, for example, be a Tesla pump. Tesla pumps deliver a fluid without having to use blades but merely by utilizing the existing viscosity of the fluid and the adhesive forces. For this purpose, a plurality of disks arranged side by side, between which the fluid is centrally introduced, are rotated via an electric motor, whereby, due to viscosity and adhesion, the fluid is tangentially delivered in the direction of rotation and radially to the outside at a rate increasing as the fluid moves to the outside. This results in a pulsation-free delivery with good efficiencies. Such a pump can have a very small design and nevertheless withstand the relatively high system pressure of the displacement counter of approximately 20 bar and temperatures of up to 150° C. Such a pump additionally operates without valves so that the system remains open when the through-flow meter is out of operation. Such a pump is inexpensive to manufacture since the manufacturing tolerances are also small.

In an embodiment of the present invention, the Tesla pump can, for example, be arranged upstream of the sensor as seen in the direction of delivery of the fluid in the bypass line, whereby, during startup, air inclusions do not reach the pump in the area of the sensor. Such air bubbles cannot be delivered by a Tesla pump due to the excessively small adhesion forces of the medium; the efficiency of the pump would otherwise be extremely reduced.

In an embodiment of the present invention, an inlet to a flow space of the Tesla pump, in which a rotor of the Tesla pump is disposed, can, for example, be arranged geodetically below the branch of the bypass line since air from the area of the inlet can rise towards the circuitous line and be discharged there. The function of the Tesla pump is thereby provided.

In an embodiment of the present invention, the bypass line section between the branch of the bypass line and the inlet to the flow space of the pump can, for example, be configured so that it continuously descends towards the inlet. Air bubbles in this bypass line section, which extends to the pump, correspondingly rise along the bypass line section towards the circuitous line and can be reliably discharged there. The function of the pump is thereby provided.

In an embodiment of the present invention, the inclination of the bypass line section between the branch and the inlet of the Tesla pump can, for example, be arranged to range between 9° and 12°. Rising of the air bubbles is hereby provided and a compact design can be maintained.

In an embodiment of the present invention, an outlet of the Tesla pump can, for example, be arranged geodetically upstream of the flow space of the Tesla pump. Air bubbles produced in the flow space during initial startup correspondingly rise to the outlet and exit the flow space so that delivery of the pump during startup is provided.

In an embodiment of the present invention, an outlet duct of the Tesla pump can, for example, be configured so that it ascends in the flow direction. A return flow of the air bubbles from the outlet to the rotor is thereby prevented.

To provide a compact and well sealed unit, the system comprises a solid body which is connected with the body in which the circuitous line is defined. A flow space of the pump, the inlet of the pump, the outlet of the pump, as well as a bypass line section between the outlet of the pump and an inlet of the sensor, as well as a circuitous line section between the outlet of the sensor and the opening into the circuitous line, are at least partially defined in the solid body. The hydraulic line sections are easy to produce as thin bores in the solid body. Additional flexible lines can be omitted.

In an embodiment of the present invention, the flow cross-section of the bypass line can, for example, be smaller than the flow cross-section of the main line and the circuitous line, and is in particular approximately 4 mm. This minimizes the effects on the flows in the circuitous line, wherein, however, an adequate pressure difference for density measurement purposes is provided. Since no flow theoretically exists in the circuitous line when the displacement device is optimally controlled, a flow due to excessive pressure differences relative to the flow cross-section of the circuitous line must be avoided. This is realized with the aid of the present bypass line without excessive pressure losses being generated in the bypass line.

A system for measuring temporally resolved through-flow processes of fluids is thus provided via which temporally resolved through-flow processes can be continuously determined with high accuracy. Additional data for controlling the system or for evaluating the measuring results, in particular with regard to the physical variables of density or viscosity of the fluid, are thereby provided without the actual measurement being negatively affected, for example, by occurring pulsations. The additionally required installation space is very small. A high pressure and temperature resistance is thereby achieved.

The system according to the present invention for measuring temporally resolved through-flow processes of fluids is described below on the basis of an exemplary embodiment illustrated in the drawings (which is not to be construed as limiting).

The system according to the present invention for measuring temporally resolved through-flow processes of fluids illustrated in FIG. 1 is composed of a through-flow meter 10 having an inlet 12 and an outlet 14 as well as a bypass line 16 via which a line section 18 of the through-flow meter 10 can be bypassed.

Via the inlet 12, a fluid to be measured, in particular a fuel, flows from a device producing a through-flow, in particular a high-pressure fuel pump, and at least one injection valve into a main line 20 of the through-flow meter 10. A rotational displacement device 22 configured as a double gear pump is arranged in this main line 20. The main line 20 ends at the outlet 14 downstream of the rotational displacement device 22. The gear pump 22 is driven by a drive motor 24 via a clutch or a gearbox.

From the main line 20, a circuitous line 26 branches off between the inlet 12 and the rotational displacement device 22, which circuitous line 26 ends at the main line 20 downstream of the between the rotational displacement device 22 and the outlet 14, and, like the main line 20, is correspondingly fluidically connected with the inlet 12 and the outlet 14. A translational pressure difference transducer 28 is disposed in the circuitous line 26 which is composed of a measuring chamber 30 and a piston 32 arranged in a freely shiftable manner in the measuring chamber 30, which has the same specific weight as the measuring fluid, i.e., the fuel, and, like the measuring chamber 30, has a cylindrical configuration. The measuring chamber 30 thus has an inner diameter which essentially corresponds to the outer diameter of the piston 32. When a pressure difference exists between the front side and the rear side of the piston 32, an excursion of the piston 32 out of its rest position takes place. The excursion of the piston 32 is therefore a measure of the existing pressure difference. At the measuring chamber 30, a path sensor 34 is arranged which is operatively connected with the piston 32 and in which a voltage depending on the magnitude of the excursion of the piston 32 is generated by the excursion of the piston 32. This path sensor 34 attached to the measuring chamber 30 is in particular a magneto-resistive sensor via which the field strength of a magnet 36 acting on the former is converted into a voltage. The magnet 36 is attached in the center of gravity of the piston 32 for this purpose. Light sensors can also be used as path sensors.

The path sensor 34 is connected with an evaluation and control unit 38 which collects the values of this path sensor 34 and transmits corresponding control signals to the drive motor 24 which, if possible, is controlled so that the piston 32 is always in a defined initial position, and the gear pump 22 thus continuously more or less compensates for the pressure difference produced at the piston 32 by the injected fluid by a delivering process. This means that in the case of an excursion of the piston 32 to the right, the rotational speed of the pump is increased as a function of the magnitude of this excursion and vice versa. The excursion of the piston 32 and/or the volume displaced by the latter in the measuring chamber 30 are converted for this purpose into a desired volume flow of the gear pump 22 and/or a rotational speed of the drive motor 24 via a transfer function, and a corresponding current is applied to the drive motor 24.

In the measuring chamber 30, a pressure sensor 40 as well as a temperature sensor 42 are arranged which continuously measure the pressures and the temperatures occurring in this area and supply them to the evaluation and control unit 38 so that any changes in the density can be taken into account when carrying out the calculation.

The measuring process is such that during the calculation of an overall through-flow to be determined in the evaluation and control unit 38, both a through-flow in the circuitous line 26 produced by a movement and/or position of the piston 32 and the volume displaced by the latter in the measuring chamber 30 as well as an actual through-flow of the gear pump 22 in a fixed time interval can be taken into account, and both through-flows can be added to determine the overall through-flow.

For example, the determination of the through-flow at the piston 32 is carried out in that in the evaluation and control unit 38, which is connected with the path sensor 34, the excursion of the piston 32 is differentiated and subsequently multiplied by the base area of the piston 32 so that a volume flow in the circuitous line 26 in this time interval is determined.

The through-flow through the gear pump 22 and thus in the main line 20 can, for example, be determined either from the determined control data for controlling the gear pump 22, or calculated via the rotational speed when the latter is directly measured at the gear pump 22, or at the drive motor 24 via optical encoders or magneto-resistive sensors.

According to the present invention, in the present exemplary embodiment, the bypass line 16 branches off the circuitous line 26 between the inlet 12 and the measuring chamber 30, the bypass line entering the circuitous line 26 again upstream of the measuring chamber 30 thus bypassing the line section 18. It would also be possible that this bypass line 16 branches off at any other position of the main line 20 or the circuitous line 26 and again enters the circuitous line 26, whereby the bypass line 16 is not allowed to bypass the rotational displacement device 22 or the translational pressure difference transducer 28.

A pump 48 delivering in a pulsation-free manner and configured as a Tesla pump as well as a sensor 50 for measuring a chemical or a physical property of the delivered fluid are connected in series one after another in the bypass line 16 between the branch 44 and the opening 46. This sensor 50 is in particular a density sensor or a viscosity sensor which is configured as a MEMS sensor measuring, for example, according to the Coriolis principle. Both the Tesla pump 48 and the sensor 50 are electrically connected with the evaluation and control unit 38 so that the measuring values of the sensor 50 can be used to improve the calculated through-flow values with the aid of the additional information concerning the density or the viscosity and to control the Tesla 48 pump. This Tesla pump 48 is required to provide a flow via the sensor 50, the measuring values of which might otherwise deviate from the actual values to be measured due to a flow stop. The pulsation-free delivery of the Tesla pump 48 further prevents the measuring values of the sensor 50 from being falsified because these sensors 50 tend to pulsate in the case of pulsating flows. Correct additional information is accordingly supplied to the evaluation and control unit 38, which information can be used both to control the rotational displacement device 22 and to calculate the through-flows to thus additionally improve the results.

The Tesla pump 48 is essentially composed of an electric motor 52 which can be configured as an electronically commutated direct-current motor, for example, as well as a rotor 54 made up of a plurality of disks 56 which are arranged one behind another at small distances to each other in a flow space 58 of the Tesla pump 48 and are driven via the electric motor 52. The rotor is rotated when current is applied to the electric motor 52.

Figure 2:
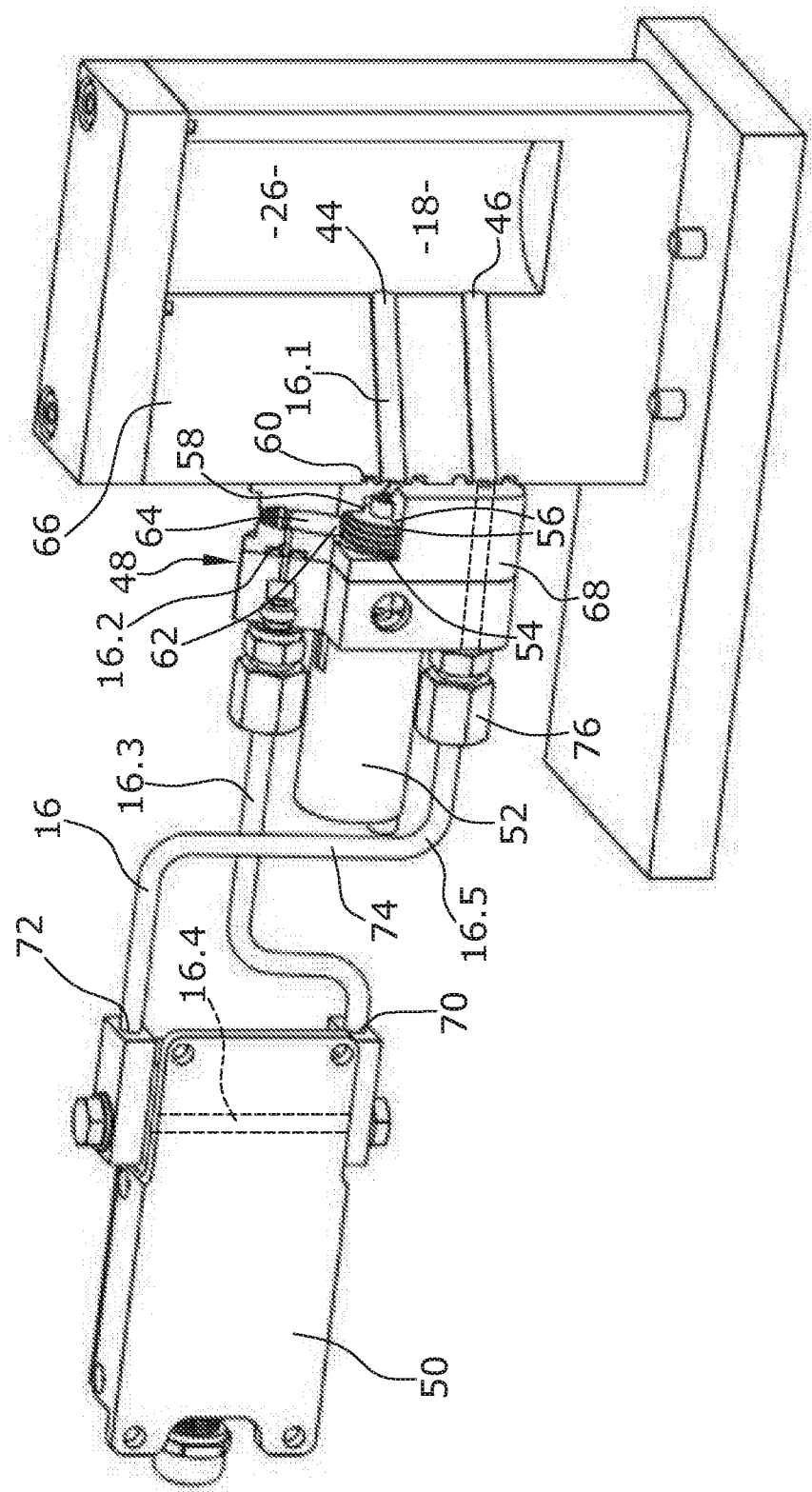
FIG. 2 shows a perspective view of a detail of a test setup of the system according to the present invention with bodies partially cut open.

FIG. 2 shows, on the basis of a test setup in which a portion of the circuitous line 26, and in particular the line section 18 is simulated by a separate cylindrical line, how, at the real through-flow meter 10, the bypass line 16 as well as the Telsa pump 48 and the sensor 50 in the bypass line 16 are connected with the here simulated circuitous line 26. The Tesla pump 48 comprises a central inlet 60 via which the fluid can flow into the flow space 58 between the disks 56. For this purpose the disks 56 comprise apertures in the inner area. By rotating the disks 56, the fluid is accelerated, due to its viscosity, by the occurring adhesion forces in the tangential direction as well as radially to the outside between the disks 56. A flow of the fluid is accordingly produced which exits the flow space 58 of the Tesla pump 48 via an outlet 62 which is arranged geodetically above the flow space 58. An outlet duct 64 extending from the outlet 62 extends tangentially to the flow space to avoid pressure losses. Due to the fact that this Tesla pump 48 does not comprise any blades, a pulsation-free flow towards the sensor 50 is produced. The through-flow characteristic zone of the Tesla pump 48 also increases essentially linearly relative to the rotational speed of the rotor 54 so that the Tesla pump 48 is easy to control.

The through-flow cross-section of the circuitous line 26 of the through-flow meter 10 is considerably larger than the cross-section of the bypass line 16, the cross-section of which is approximately 4 mm so that relatively small flow rates are required to generate a necessary pressure difference. The pulsation-free delivery of the Tesla pump 48 as well as these small flow rates provide that an effect on the control circuit of the rotational displacement device 22 and the translational pressure difference transducer 28 due to undesired flows or pulsations is virtually non-existent. This diameter has also turned out to be advantageous to discharge air inclusions which are in particular produced during initial startup.

Further measures are taken to prevent measuring errors caused by air inclusions in the system. A bypass line section 16.1, which extends from the branch 44 to the central inlet 60 into the flow space 58 and thus to the rotor 54 of the Tesla pump 48, is inclined by an angle of approximately 11° towards the central inlet 60. Air inclusions in this bypass line section 16.1 can consequently rise to the circuitous line 26 and be discharged there. The design of the outlet duct 64 of the Tesla pump 48, which is arranged in the geodetically upper area and extends further upwards, also results in the air bubbles rising out of the flow space 58 of the Tesla pump 48. Flow space 58 is accordingly filled with fluid when the Tesla pump 48 is out of operation, whereby a delivery by the Tesla pump 48 is provided in which air that cannot otherwise be discharged would collect in the interior of the rotor 54.

The flow conduction and the line run are such that at first at the branch 44, the first bypass line section 16.1 extending to the central inlet 60 of the Tesla pump 48 branches off the circuitous line 26 in a downward direction at an angle of 11°. This bypass line section 16.1 is defined in a body 66 in which a section of the circuitous line 26 is also defined. To this body 66, a solid body 68 is attached in which the central inlet 60 to the Tesla pump 48 as well as its flow space 58 are defined. The outlet duct 64 of the Tesla pump 48 also branches off the flow space 58 in this solid body 68. The outlet duct 64 enters another approximately horizontally extending bypass line section 16.2, which enters a bypass line section 16.3 configured as a connecting pipe extending to the sensor 50, which connecting pipe 16.3 is bent downwards so that an inlet 70 is arranged geodetically below the sensor 50. A subsequent bypass line section 16.4 extends approximately vertically through the sensor to its outlet 72 arranged above it. From the outlet 72, a bypass line section 16.5 extends which is at first defined by a bent pipe 74 the connecting stub 76 of which is attached to the solid body 68 geodetically below the flow space 58, and continuous to extend in the interior of the solid body 68 as well as the body 66 up to the opening 46 which is correspondingly arranged geodetically below the branch.

It can be seen that the line section 18 of the circuitous line 26 is bypassed by the bypass line 16, wherein, during delivery by the Tesla pump 48, a circulation flow from the opening 46 of the bypass line 16 to the branch 44 via the line section 18 is produced, in particular since in the ideal case the gear pump 22 completely compensates for a pressure difference via the piston 32, whereby, in the ideal case, no flow occurs in the circuitous line 26.

A flow which is produced in the bypass line 16 by a rotation of the rotor 54 of the Tesla pump 48 correspondingly moves along these bypass line sections 16.1-16.5, the line section 18, and through the sensor 50, the measuring values of which are then transmitted to the evaluation and control unit. The through-flow meter thus continuously calculates temporally highly resolved through-flow process with a high accuracy, wherein, in comparison to conventional designs, additional data to control the system or to evaluate the measuring results, in particular with regard to the physical variables of density and viscosity of the fluid, are provided. Both an adequate flow for providing the function of the density sensor is hereby provided and effects on the through-flow meter are avoided since excessively large flow rates and occurring pulsations are precluded. The system is of a very compact design and offers a high pressure and temperature resistance of up to 20 bar and 150° C. Precautionary measures for providing the function of the pump by discharging disturbing air bubbles were also taken. The density sensor and the pump can be operated both continuously and at defined time intervals and transmit their data to the evaluation and control unit.

It should be appreciated that the invention is not limited to the described exemplary embodiment, but that various modifications are possible. Other continuously operating through-flow meters can generally be used, or the bypass line can bypass the corresponding line section at another position of the through-flow meter.

Although the present invention has been described and illustrated with reference to specific illustrative embodiments, it is not intended that the present invention be limited to these illustrative embodiments. Those skilled in the art will recognize that variations and modifications can be made without departing from the true scope of the present invention as defined by the claims that follow. It is therefore intended to include within the present invention all such variations and modifications as fall within the scope of the appended claims and equivalents thereof.

What is claimed is:

1. A system for measuring temporally resolved through-flow processes of a fluid, the system comprising:
 an inlet;
 an outlet;
 a bypass line comprising a pump and a sensor connected in series, the sensor being configured to measure a physical property or a chemical property of the fluid; and a through-flow meter arranged between the inlet and the outlet, the through-flow meter comprising a line section, wherein, the line section of the through-flow meter is configured to be passed by the fluid via the bypass line in which the pump and the sensor are connected in series.

2. A system for measuring temporally resolved through-flow processes of a fluid, the system comprising:
an inlet;
a main line comprising a line section;
an outlet fluidically connected with the inlet via the main line;
a displacement device configured to be driven in and arranged in the main line;
a circuitous line which branches off the main line between the inlet and the displacement device and to enter the main line between the displacement device and the outlet;
a pressure difference transducer arranged in the circuitous line;
an evaluation and control unit configured to control the displacement device as a function of a pressure difference prevailing at the pressure difference transducer; and
a bypass line comprising a pump and a sensor connected in series, the sensor being configured to measure a physical property or a chemical property of the fluid, the bypass line being arranged to branch off from the main line or from the circuitous line and to end at a same side of the displacement device and the pressure difference transducer so as to bypass the line section of the main line or the circuitous line from which the bypass line branches off.

3. The system as recited in claim 2, wherein the bypass line branches off and ends at the circuitous line between the inlet and the pressure difference transducer.

4. The system as recited in claim 2, wherein the sensor is a density sensor or a viscosity sensor.

5. The system as recited in claim 4, wherein the pump is configured to deliver in a pulsation-free manner.

6. The system as recited in claim 5, wherein the pump is a Tesla pump.

7. The system as recited in claim 6, wherein the Tesla pump is arranged upstream of the sensor as seen in a direction of delivery.

8. The system as recited in claim 6, wherein,
the bypass line comprises a branch,
the Tesla pump comprises an inlet to a flow space in which a rotor is arranged, and
the inlet is arranged geodetically below the branch of the bypass line.

9. The system as recited in claim 8, wherein, the bypass line comprises a first bypass line section which is defined between the branch and the inlet to the flow space of the Tesla pump so that the first bypass line section comprising an inclination which continuously descends towards the inlet of the Tesla pump.

10. The system as recited in claim 9, wherein the inclination of the first bypass line section between the branch and the inlet of the Tesla pump is between 9° and 12°.

11. The system as recited in claim 8, wherein the Tesla pump further comprises an outlet, the outlet being arranged geodetically above the flow space of the Tesla pump.

12. The system as recited in claim 11, wherein the Tesla pump further comprises an outlet duct which is configured to ascend in a direction of delivery.

13. The system as recited in claim 12, wherein,
the sensor comprises a sensor inlet and a sensor outlet, and
the circuitous line further comprises an opening,
the system further comprising:
a body in which the circuitous line is defined;
a second bypass line section arranged between the outlet duct of the Tesla pump and the sensor inlet;
a third bypass line section arranged between the sensor outlet and the opening into the circuitous line; and
a solid body connected with the body, the solid body being configured so that the flow space of the Tesla pump, the inlet of the Tesla pump, the outlet duct of the Tesla pump, the second bypass line section, the sensor inlet, and the third bypass line section are each at least partially defined thereby.

14. The system as recited in claim 2, wherein,
the bypass line comprises a through-flow cross-section,
the circuitous line comprises a through-flow cross-section,
the main line comprises a through flow-cross section, and
the through-flow cross section of the bypass line is smaller than the through-flow cross-section of the main line and the through-flow cross section of the circuitous line.

* * * * *